United States Patent
Esteller et al.

(10) Patent No.: US 11,583,678 B2
(45) Date of Patent: Feb. 21, 2023

(54) NEUROSTIMULATION SYSTEM WITH NEURODEGENERATIVE DISEASE DETECTION

(71) Applicant: Boston Scientific Neuromodulation Corporation, Valencia, CA (US)

(72) Inventors: Rosana Esteller, Santa Clarita, CA (US); Joseph M. Bocek, Seattle, WA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 183 days.

(21) Appl. No.: 16/942,314

(22) Filed: Jul. 29, 2020

(65) Prior Publication Data

US 2021/0031043 A1 Feb. 4, 2021

Related U.S. Application Data

(60) Provisional application No. 62/882,272, filed on Aug. 2, 2019.

(51) Int. Cl.
*A61N 1/36* (2006.01)
*A61N 1/04* (2006.01)
(Continued)

(52) U.S. Cl.
CPC ............ *A61N 1/36082* (2013.01); *A61B 5/24* (2021.01); *A61N 1/0456* (2013.01); *A61N 1/0551* (2013.01); *A61N 1/36031* (2017.08)

(58) Field of Classification Search
CPC ............... A61N 1/0551; A61N 1/0456; A61N 1/36132; A61N 1/36135; A61N 1/36031; A61N 1/36082
See application file for complete search history.

(56) References Cited

U.S. PATENT DOCUMENTS 7,539,536 B2  5/2009  Schwartz et al.
9,265,431 B2  2/2016  Hincapie Ordonez et al.
(Continued)

OTHER PUBLICATIONS

Harrar, Sari, "Patient Guide To Diabetic Neuropathy, Diabetic Neuropathy: Causes and Symptoms", Endocrineweb, Updated on: May 2, 2017, (2017), 3 pgs.
(Continued)

*Primary Examiner* — Alyssa M Alter
(74) *Attorney, Agent, or Firm* — Schwegman Lundberg & Woessner, P.A.

(57) ABSTRACT

An example of a system for delivering neurostimulation energy to a patient using a plurality of electrodes may include a stimulation circuit and a sensing circuit. The stimulation circuit may be configured to deliver the neurostimulation energy using stimulation electrodes selected from the plurality of electrodes and to control the delivery of the neurostimulation energy. The sensing circuit may be configured to receive one or more neural signals from sensing electrodes selected from the plurality of electrodes and may include a signal processing circuit. The signal processing circuit may include a detection circuit and an analysis circuit. The detection circuit may be configured to detect one or more attributes of neural responses from the received one or more neural signals. The analysis circuit may be configured to analyze the detected one or more attributes of the neural responses for one or more indications of a neurodegenerative disease.

20 Claims, 12 Drawing Sheets

(51) Int. Cl.
*A61N 1/05* (2006.01)
*A61B 5/24* (2021.01)

(56) References Cited

U.S. PATENT DOCUMENTS

| | | |
|---|---|---|
| 9,302,112 B2 | 4/2016 | Bornzin et al. |
| 9,399,132 B2 | 7/2016 | Parramon et al. |
| 9,949,651 B2 | 4/2018 | Stone et al. |
| 2017/0014625 A1* | 1/2017 | Rosenbluth .......... A61N 1/0476 |
| 2017/0079598 A1 | 3/2017 | Stolen et al. |

OTHER PUBLICATIONS

Said, Gerard, "Diabetic Neuropathy—A Review", Nat Clin Pract Neurol., 3(6), (2007), 331-340.

Toft, Daniel J., "Patient Guide To Diabetic Neuropathy, Diabetic Neuropathy Symptoms", Endocrineweb, Updated on: May 15, 2017, (2017), 5 pgs.

Toft, Daniel J., "Patient Guide To Diabetic Neuropathy, Types of Diabetic Neuropathy", Endocrineweb, Updated on: Feb. 8, 2017, (2012), 2 pgs.

\* cited by examiner

NEUROSTIMULATION SYSTEM WITH NEURODEGENERATIVE DISEASE DETECTION

CLAIM OF PRIORITY

This application claims the benefit of priority under 35 U.S.C. § 119(e) of U.S. Provisional Patent Application Ser. No. 62/882,272, filed on Aug. 2, 2019, which is herein incorporated by reference in its entirety.

TECHNICAL FIELD

This document relates generally to medical devices and more particularly to an implantable neurostimulation system that delivers stimulation and senses nervous system responses to detect neurodegenerative diseases and monitor their progression.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

Patients treated with implantable neurostimulation system may have nerve diseases that may or may not be targeted by the treatment delivered from the system. For example, many patients receiving SCS or DBS have neurodegenerative diseases such as Alzheimer's disease, Parkinson's disease, multiple sclerosis, peripheral neuropathies, diabetic neuropathy, chronic pain, and glaucoma. A patient diagnosed with such a neurodegenerative disease may need to be treated by neurostimulation deliverable using the implantable neurostimulation system and/or one or more other therapies.

SUMMARY

An example (e.g., "Example 1") of a system for delivering neurostimulation energy to a patient using a plurality of electrodes may include a stimulation circuit and a sensing circuit. The stimulation circuit may be configured to deliver the neurostimulation energy using stimulation electrodes selected from the plurality of electrodes and to control the delivery of the neurostimulation energy. The sensing circuit may be configured to receive one or more neural signals from sensing electrodes selected from the plurality of electrodes and may include a signal processing circuit. The signal processing circuit may include a detection circuit and an analysis circuit. The detection circuit may be configured to detect one or more attributes of neural responses from the received one or more neural signals. The analysis circuit may be configured to analyze the detected one or more attributes of the neural responses for one or more indications of a neurodegenerative disease.

In Example 2, the subject matter of Example 1 may optionally be configured such that the analysis circuit is further configured to generate a disease alert in response to the neurodegenerative disease being indicated as an outcome of the analysis.

In Example 3, the subject matter of any one or any combination of Examples 1 and 2 may optionally be configured to further include a memory circuit configured to store the detected one or more attributes of the neural responses, and such that the analysis circuit is further configured to analyze the detected one or more attributes of the neural responses over time for a level of disease progression in the neurodegenerative disease.

In Example 4, the subject matter of Example 3 may optionally be configured such that the analysis circuit is further configured to generate a disease progression alert in response to the level of disease progression being above a threshold level.

In Example 5, the subject matter of any one or any combination of Examples 1 to 4 may optionally be configured such that the sensing circuit is configured to receive the one or more neural signals during the delivery of the neurostimulation energy.

In Example 6, the subject matter of any one or any combination of Examples 1 to 5 may optionally be configured such that the stimulation circuit is configured to deliver neurostimulation pulses, and the detection circuit is configured to detect the neural responses each evoked by a pulse of the neurostimulation pulses.

In Example 7, the subject matter of any one or any combination of Examples 1 to 6 may optionally be configured to include an implantable stimulator including the stimulation circuit and the sensing circuit.

In Example 8, the subject matter of Example 7 may optionally be configured such that the stimulation circuit is configured to deliver spinal cord stimulation (SCS), and the sensing circuit is configured to sense one or more electrospinogram (ESG) signals.

In Example 9, the subject matter of any one or any combination of Examples 7 and 8 may optionally be configured to further include a transcutaneous electrical nerve stimulation (TENS) device including surface stimulation electrodes configured to be attached onto the patient. The TENS device is configured to deliver external stimulation pulses using the surface stimulation electrodes, and the detection circuit is further configured to detect the neural responses each evoked by a pulse of the external stimulation pulses.

In Example 10, the subject matter of any one or any combination of Examples 1 to 9 may optionally be configured such that the detection circuit is configured to detect a neural conduction velocity (NCV) of the neural responses.

In Example 11, the subject matter of Example 10 may optionally be configured such that the detection circuit is configured to detect the NCV by detecting a time interval during which a detected feature of the neural responses travels a known distance.

In Example 12, the subject matter of Example 11 may optionally be configured such that the detection circuit is configured to detect the NCV by detecting a time interval between a response of the detected neural responses and a stimulus of the delivered neurostimulation energy that evoked that response.

In Example 13, the subject matter of any one or any combination of Examples 10 to 12 may optionally be configured such that the analysis circuit is configured to compare the detected NCV to an NCV threshold range for an NCV-based indication of the one or more indications of one or more neurodegenerative diseases.

In Example 14, the subject matter of any one or any combination of Examples 1 to 13 may optionally be configured such that the detection circuit is configured to detect a morphology of the neural responses. The morphology to be detected includes a neural response waveform or one or more morphological parameters representing the neural response waveform.

In Example 15, the subject matter of Example 14 may optionally be configured such that the analysis circuit is configured to compare the detected morphology to a stored template morphology for a morphology-based indication of the one or more indications of one or more neurodegenerative diseases.

An example (e.g., "Example 16") of a method for operating a system configured for delivering neurostimulation energy to a patient using a plurality of electrodes is also provided. The method may include delivering the neurostimulation energy using stimulation electrodes selected from the plurality of electrodes, controlling the delivery of the neurostimulation energy, receiving one or more neural signals from sensing electrodes selected from the plurality of electrodes, detecting one or more attributes of neural responses from the one or more neural signals, and analyzing the detected one or more attributes of the neural responses for one or more indications of a neurodegenerative disease.

In Example 17, the subject matter of Example 16 may optionally further include performing the method for a preventive check of health of the patient's nervous system.

In Example 18, the subject matter of any one or any combination of Examples 16 and 17 may optionally further include performing the method repeatedly over time to track progression of the neurodegenerative disease.

In Example 19, the subject matter of delivering the neurostimulation energy as found in any one or any combination of Examples 16 to 18 may optionally include delivering the neurostimulation pulses from an implantable stimulator coupled to the stimulation electrodes selected from the plurality of electrodes.

In Example 20, the subject matter of delivering the neurostimulation energy as found in any one or any combination of Examples 16 to 18 may optionally include delivering the neurostimulation pulses from at least one of an implantable stimulator coupled to the stimulation electrodes selected from the plurality of electrodes or a transcutaneous electrical nerve stimulation (TENS) device including surface stimulation electrodes configured to be attached onto the patient.

In Example 21, the subject matter of detecting the one or more attributes of the neural responses as found in any one or any combination of Examples 16 to 20 may optionally include detecting a neural conduction velocity (NCV).

In Example 22, the subject matter of detecting the NCV as found in Example 21 may optionally include detecting at least one of a time interval during which a detected feature of the neural responses travels a known distance or a time interval between a response of the detected neural responses and a stimulus of the delivered neurostimulation energy that evoked that response, and the subject matter of analyzing the detected one or more attributes of the neural responses as found in Example 21 may optionally include comparing the detected NCV to an NCV threshold range for an NCV-based indication of the one or more indications of one or more neurodegenerative diseases.

In Example 23, the subject matter of detecting the one or more attributes of the neural responses as found in any one or any combination of Examples 16 to 22 may optionally include detecting a morphology of the neural responses. The morphology to be detected includes a neural response waveform or one or more morphological parameters representing the neural response waveform.

In Example 24, the subject matter of wherein analyzing the detected one or more attributes of the neural responses as found in Example 23 may optionally include comparing the detected morphology to a stored template morphology for a morphology-based indication of the one or more indications of one or more neurodegenerative diseases.

An example (e.g., "Example 25") of a non-transitory computer-readable storage medium including instructions, which when executed by a machine, cause the machine to perform a method for operating a system configured for delivering neurostimulation energy to a patient using a plurality of electrodes is also provided. The method may include delivering the neurostimulation energy using stimulation electrodes selected from the plurality of electrodes, controlling the delivery of the neurostimulation energy, receiving one or more neural signals from sensing electrodes selected from the plurality of electrodes, detecting one or more attributes of neural responses from the one or more neural signals, and analyzing the detected one or more attributes of the neural responses for one or more indications of a neurodegenerative disease.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
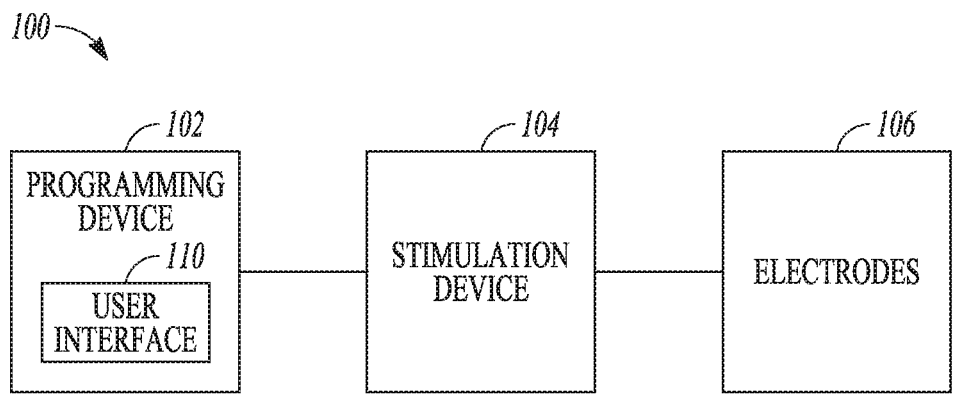
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can deliver neurostimulation energy to a patient and can sense one or more neural signals for detecting one or more indications of neuroregenerative diseases of the patient. The neurostimulation system can include an implantable stimulator that delivers the neurostimulation energy to the patient through an implantable lead with an array of electrodes. The implantable stimulator can sense one or more neural signals using electrodes selected from the array of electrodes of the implantable lead and analyze neural responses in the sensed sense one or more neural signals for one or more indications of the neuroregenerative diseases and their progression.

In various embodiments, the implantable stimulator can deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. Many patients receiving DBS and SCS therapies have degenerative diseases, particularly neurodegenerative diseases (also referred to as neuronal degenerative diseases or degenerative nerve diseases) such as Alzheimer's disease, Parkinson's disease, multiple sclerosis, peripheral neuropathies, diabetic neuropathy, chronic pain, and glaucoma. Many of these neurodegenerative diseases alter nerve conduction velocity (NCV) and morphology of the neural responses. For example, nerve conduction study (NCS) can detect NCV alternations to predict clinical diabetic neuropathy (DN) before the patient experience any symptoms and before abnormalities are detected using other DN diagnostic tools such as reflex, pressure sense, and vibration perception threshold (VPT).

The present subject matter provides a stimulation device with sensing capabilities for determining such alterations in NCV, morphology, and/or other attributes of neural responses that may indicate neurodegenerative diseases. For example, an implantable stimulator for SCS or DBS can be equipped with sensing capabilities to sense neural responses and detect speed of transmission of the neural responses and/or morphology of the neural responses. This allows for monitoring of disease progression and/or preventive health check for the patient carrying the implantable stimulator.

In this document, unless noted otherwise, a "patient" includes a person receiving treatment delivered from, and/or monitored using, a neurostimulation system according to the present subject matter, and a "user" includes a physician or other caregiver who examines and/or treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for SCS applications. While an SCS system is illustrated and discussed as an example, the present subject matter applies to any neurostimulation system with electrodes placed in locations suitable for sensing one or more neural signals from which indications of degenerative and/or other nerve diseases can be detected and monitored.

Figure 2:
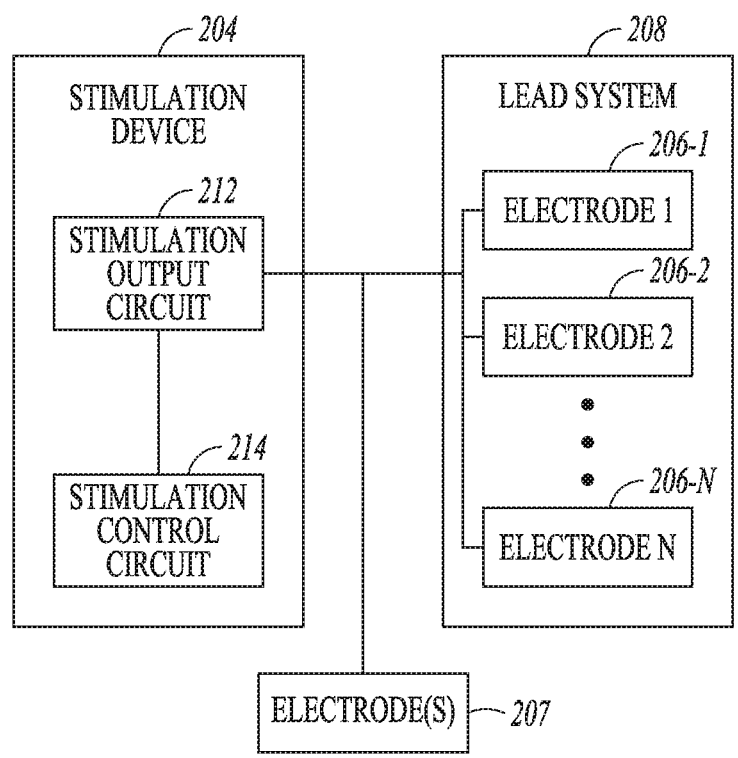
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and optionally electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Lead and electrode configurations are illustrated in this document as examples and not limitations. For example, various embodiments can use paddle electrodes, cuff electrodes, and other electrodes suitable for delivering neurostimulation.

Figure 3:
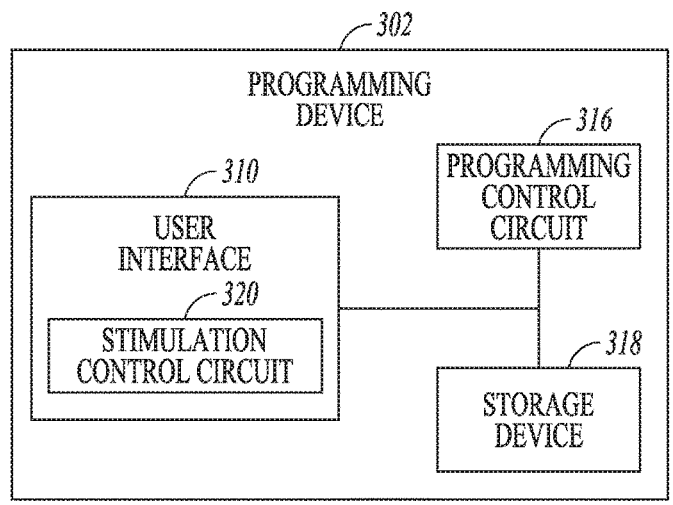
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit can include, but is not limited to, a microprocessor or a portion thereof, a microcontroller or portions thereof, and/or a programmable logic circuit or a portion thereof.

Figure 4:
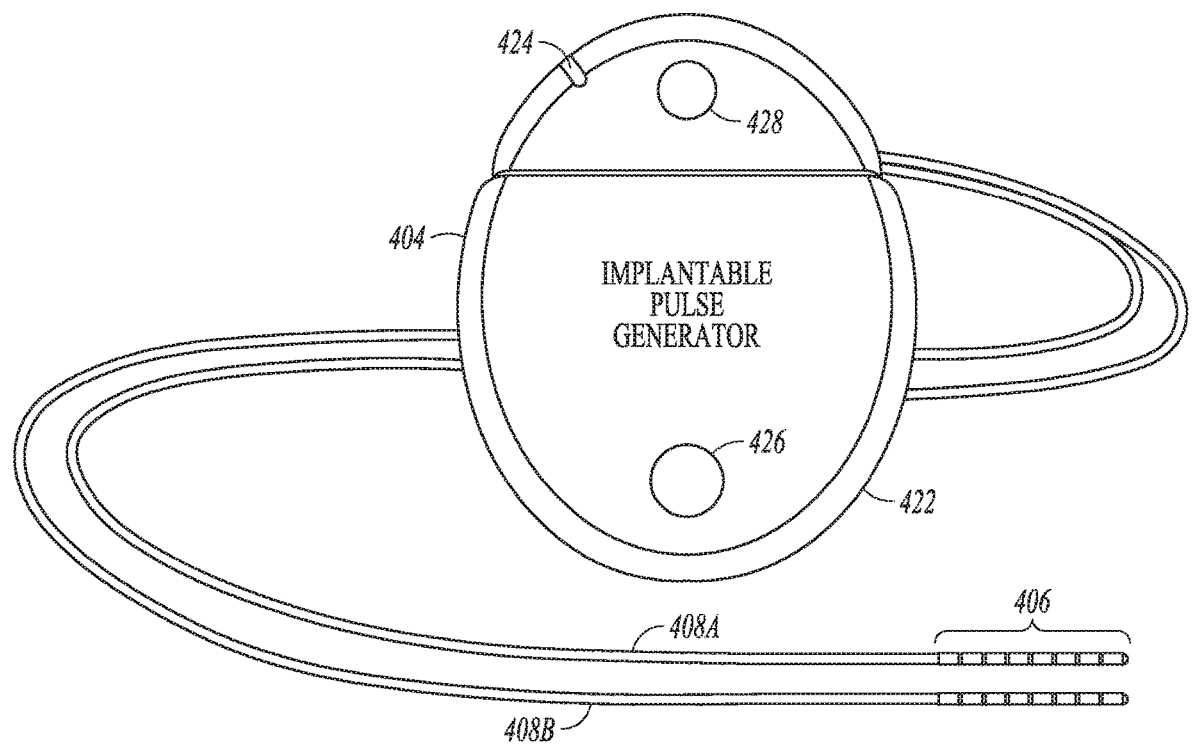
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to target nerve cells in the subject's spinal cord.

Figure 5:
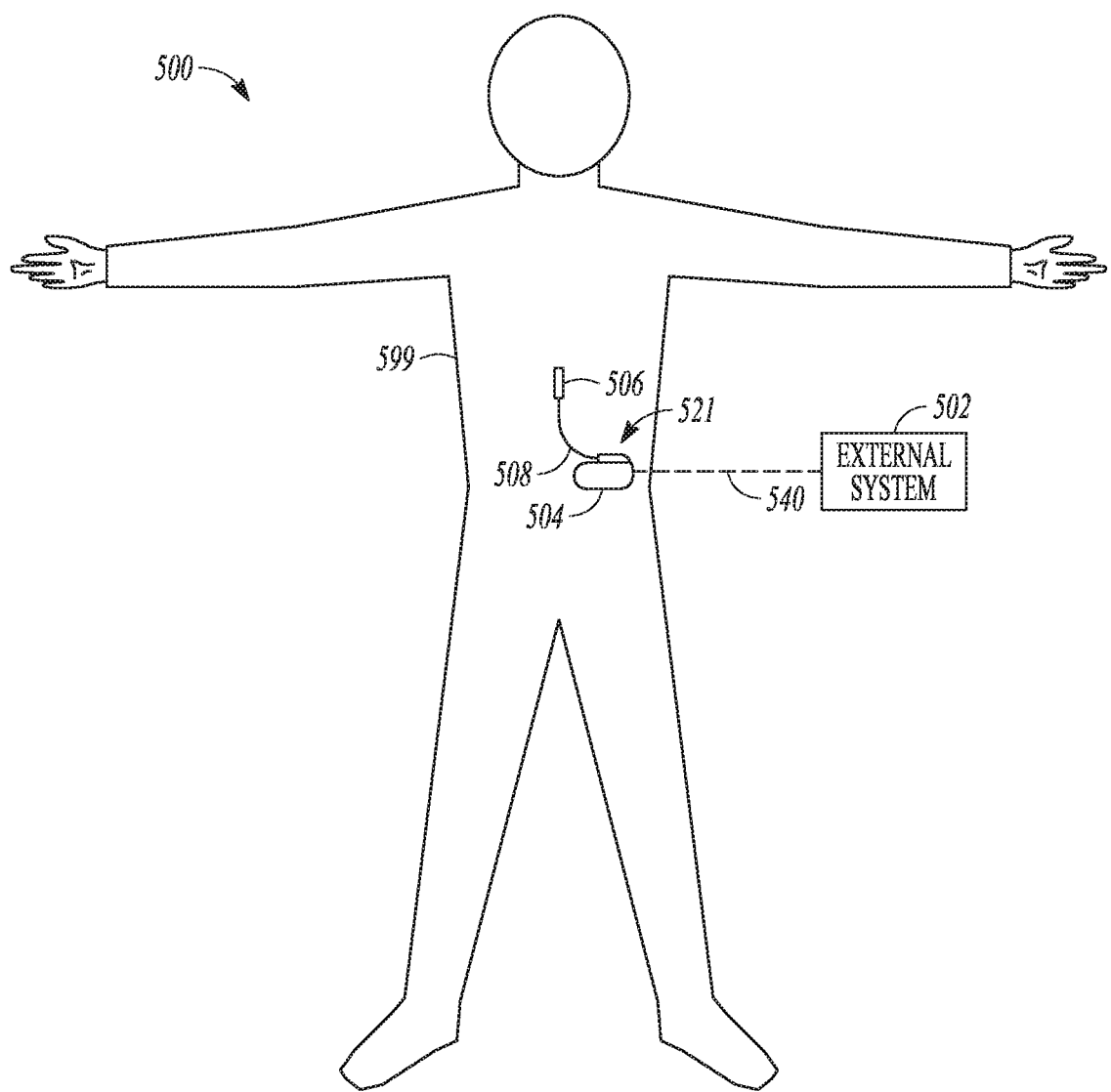
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external system 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
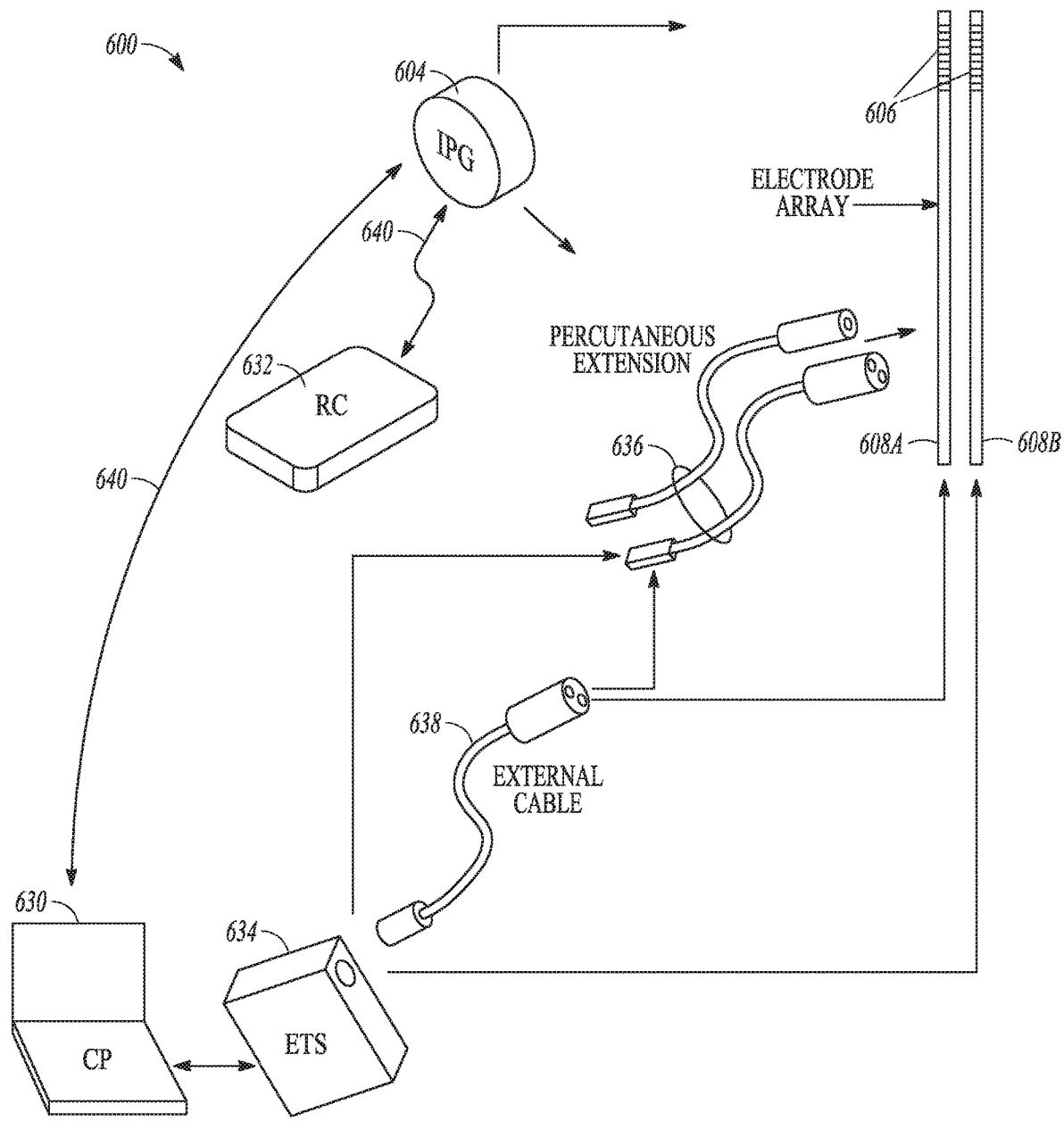
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device configured for ambulatory use and may be used as a preliminary stimulator after leads 408A and 408B have been implanted and used prior to stimulation with IPG 604 to test the patient's responsiveness to the stimulation that is to be provided by IPG 604. ETS 634 may include cable connectors allowing it to readily interface the proximal end of external leads that are chronic use, and may include replaceable batteries.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
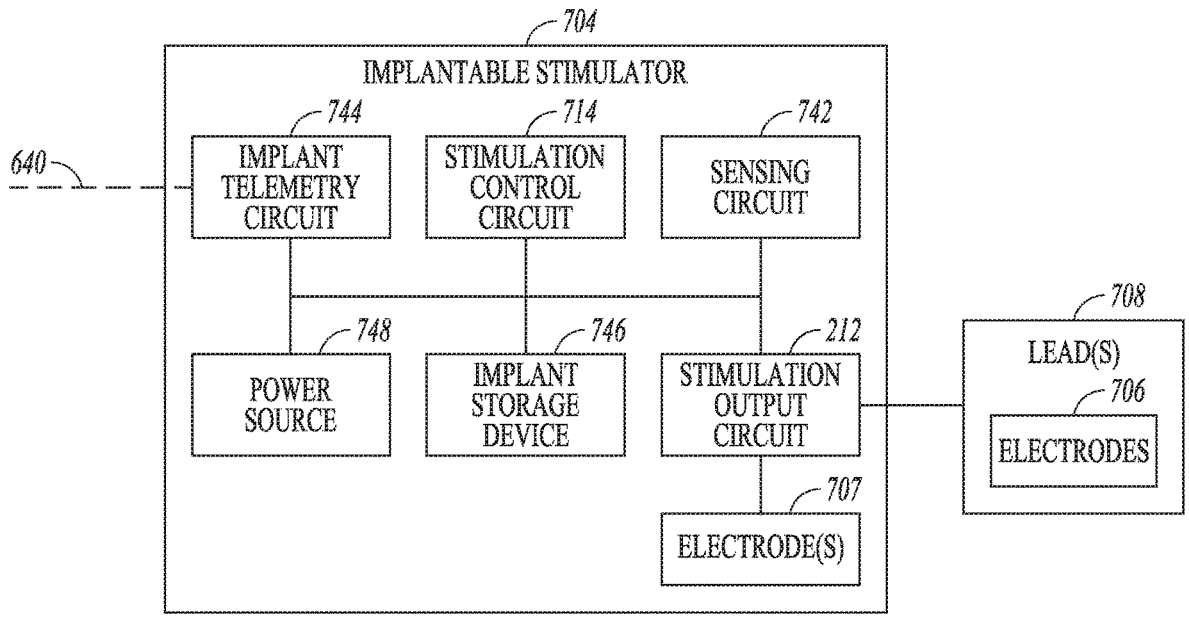
FIG. 7 illustrates an embodiment of an implantable stimulator and one or more implantable leads of a neurostimulation system, such as the neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. In various embodiments, sensing circuit 742 senses one or more neural signals and detects one or more indications of a neurodegenerative disease, as further discussed with reference to FIGS. 9-16. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s)

707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
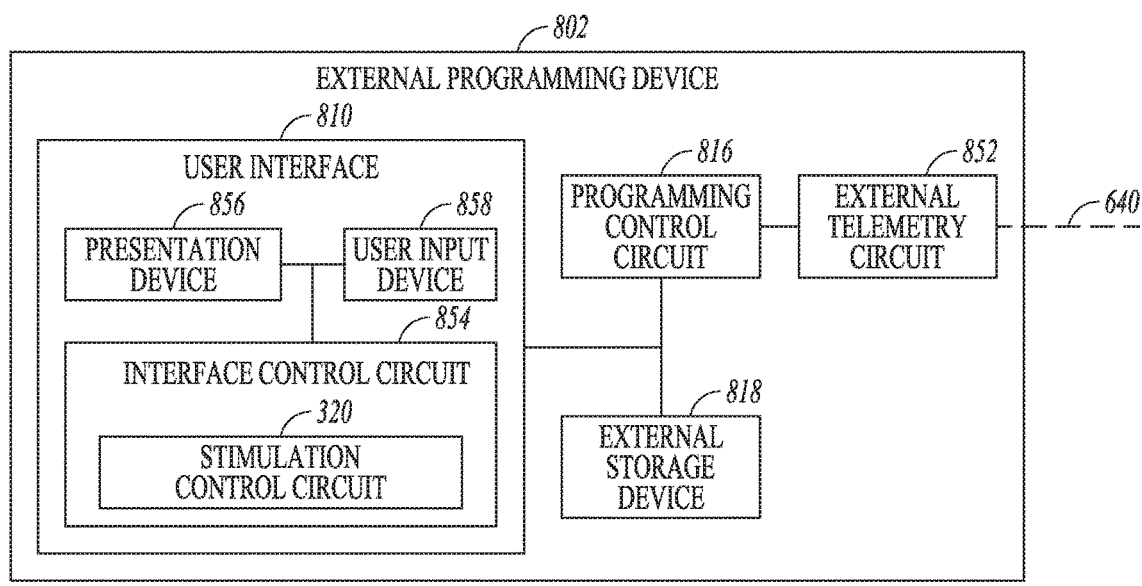
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
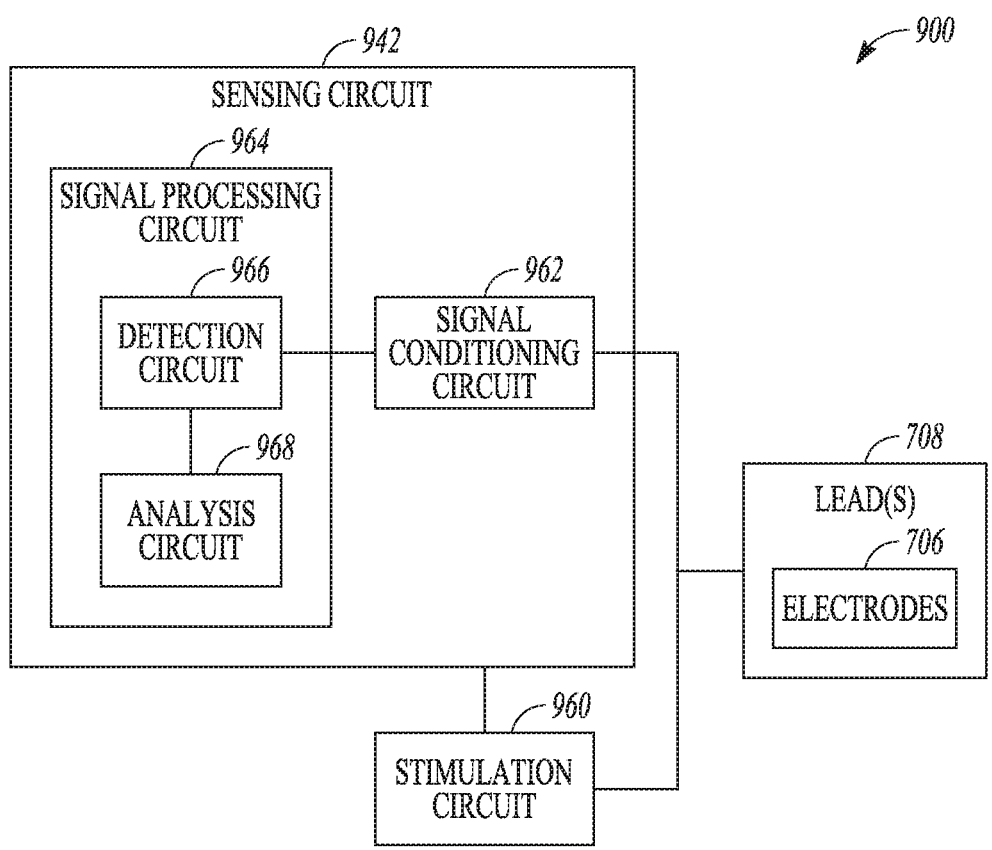
FIG. 9 illustrates an embodiment of a neurostimulation system with disease detection capabilities.

FIG. 9 illustrates an embodiment of a neurostimulation system 900 with disease detection capabilities. System 900 includes one or more leads 708 with electrodes 706 and can deliver neurostimulation energy to the patient using one or more electrodes selected from electrodes 706. System 900 includes a stimulation circuit 960 and a sensing circuit 942. Stimulation circuit 960 can deliver the neurostimulation energy using stimulation electrodes selected from electrodes 706 and control the delivery of the neurostimulation energy. Sensing circuit 942 includes a signal conditioning circuit 962 and a signal processing circuit 964. Signal conditioning circuit 962 can receive one or more neural signals from sensing electrodes selected from the plurality of electrodes and can pre-condition the one or more neural signals for processing (e.g., using amplification and filtering). Signal processing circuit 964 includes a detection circuit 966 and an analysis 968. Detection circuit 96 can detect one or more attributes of neural responses from the pre-conditioned one or more neural signals. The analysis circuit 968 can analyze the detected one or more attributes of the neural responses for one or more indications of a neurodegenerative disease.

The neural responses can include spontaneous and/or evoked neural responses. The evoked neural responses include neural responses evoked by the delivery of the neurostimulation energy from stimulation circuit 960. In various embodiments, the neurostimulation energy can be delivered in the form of electrical neurostimulation pulses, and the neural responses can each include a response evoked by an electrical neurostimulation pulse.

Figure 10:
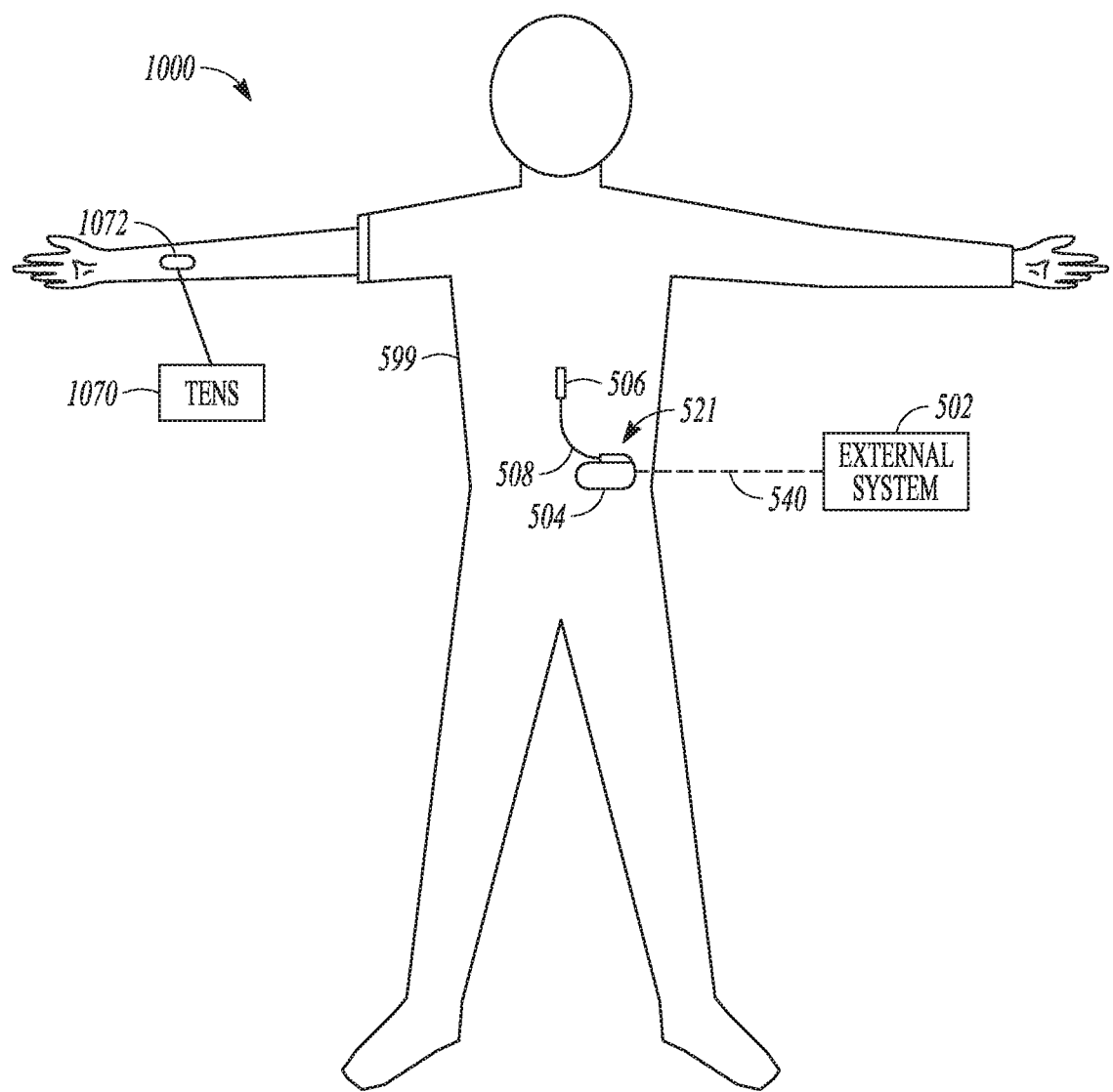
FIG. 10 illustrates an embodiment of a neurostimulation system including an IPG, an implantable lead system, and optionally a transcutaneous electrical nerve stimulation (TENS) unit arranged to provide neurostimulation to, and sense neural signals, from a patient.

FIG. 10 illustrates an embodiment of a neurostimulation system 1000 that can represent an example of system 500 configured to include disease detection capabilities such as those of system 900. As illustrated in FIG. 10, system 1000 is configured as an SCS system capable of sensing diagnostic indicators from the spinal cord and optionally also peripheral nerves.

As shown in FIG. 10, system 100 can optionally include a transcutaneous electrical nerve stimulation (TENS) unit 1070 that can deliver neurostimulation energy using surface stimulation electrodes 1072. Electrodes 1072 can be configured as one or more skin patches for attaching to the patient's skin). In various embodiments, the neural responses analyzed for the one or more indications of the neurodegenerative disease can be evoked by the neurostimulation energy (e.g., electrical neurostimulation pulses) delivered from IPG 504 and/or TENS unit 1070. When IPG 504 and lead 508 with electrodes 506 are placed for SCS, the neural responses can be analyzed for one or more indications of a neurodegenerative disease in one or more fibers of the spinal cord. TENS unit 1070 is used, for example, to allow for detection and analysis of neural responses of nerves not accessible using electrodes 506 of implantable lead 508. Electrodes 1072 can be placed on the patient over a target nerve for delivering the neurostimulation energy to the target nerve, such that the neural responses can be analyzed for one or more indications of a neurodegenerative disease in one or more peripheral nerves.

In various embodiments, TENS unit 1070 may include a device customized for integration into system 1000 to meet isolation and communication requirements. Time synchronization between TENS unit 1070 and implantable system 521 can be required for measuring one or more attributes of the neural responses to stimulation delivered by TENS unit 1070. This requires establishment of a timing relationship between external and implanted devices such as between TENS unit 1070 and IPG 504. In one embodiment, TEMS unit 1070 sends a timing signal to IPG 504 via telemetry link 540 with a transmission timestamp relative to a real time clock of TEMS unit 1070. IPG 504 marks the time of reception of the timing signal with a reception timestamp using a real time clock of IPG 504. IPG 504 then determines a time offset based on the transmission and reception timestamps. The telemetry delay can be calibrated a priori. The time offset can also be determined by a reverse process. That is, IPG 504 sends a timing signal to TEMS unit 1070 via telemetry link 540 with a transmission timestamp relative to a real time clock of IPG 504, and TEMS unit 1070 marks the time of reception of the timing signal with a reception timestamp using a real time clock of TEMS unit 1070. In another embodiment, external system 502 controls timing of measuring the one or more attributes of neural responses to stimulation delivered from TENS unit 1070 and timestamps each stimulus delivered from TENS unit 1070. The timestamps can each be generated by electrically sensing when a stimulus is delivered when TENS unit 1070 delivers stimuli autonomously or by controlling timing of delivery of each stimulus from TENS unit 1070.

Figure 11:
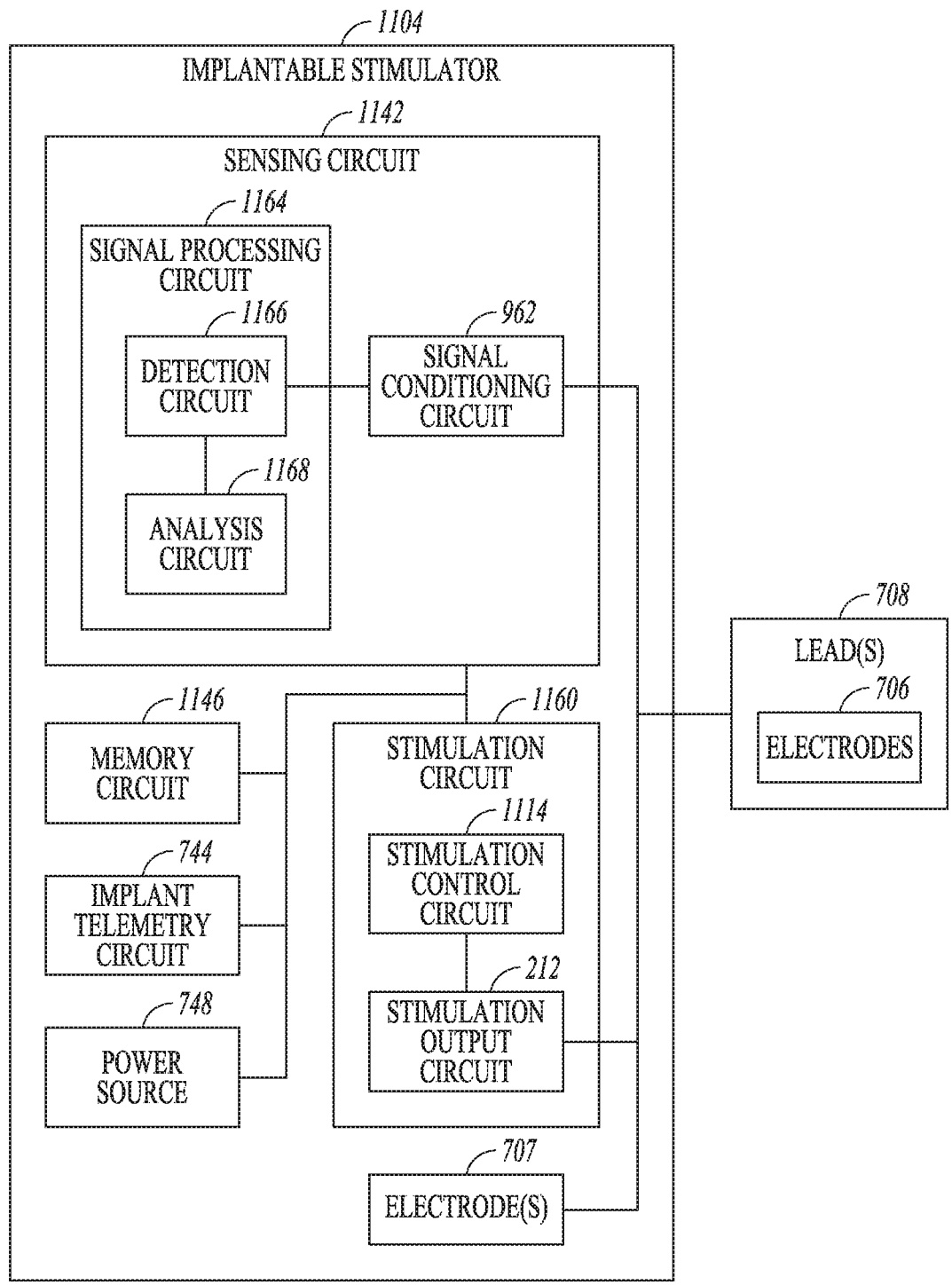
FIG. 11 illustrates an embodiment of an implantable stimulator, one or more implantable leads, and optionally a TENS unit, of a neurostimulation system, such as the neurostimulation system of FIG. 10.

FIG. 11 illustrates an embodiment of an implantable stimulator 1104 and lead(s) 708. Implantable stimulator 1104 represents an example of IPG 504 or implantable stimulator 704 that is configured for operation in neurostimulation system 1000 (i.e., with disease detection capabilities). Implantable stimulator 1104 can include a stimulation circuit 1160, a sensing circuit 1142, a memory circuit 1146, implant telemetry circuit 744, power source 748, and electrode(s) 707. For example, implantable stimulator 1104 can be based on implantable stimulator 704 with sensing circuit 742 configured to provide the disease detection capabilities and, if necessary, stimulation control circuit 714 configured to control the delivery of the neurostimulation energy for coordinating with the disease detection and/or adjustment of the delivery based on an outcome of the disease detection.

Stimulation circuit 1160 represents an example of stimulation circuit 960 and includes stimulation output circuit 212 and a stimulation control circuit 1114. When implantable stimulator 1104 is connected to lead(s) 708, stimulation output circuit 212 is coupled to electrodes 706 and can deliver the neurostimulation energy (e.g., electrical neurostimulation pulses) using one or more stimulation electrodes selected from electrodes 706. In various embodiments, stimulation output circuit 212 can deliver the neurostimulation energy through one or more stimulation channels each including a set of stimulation electrodes selected to deliver a portion of the neurostimulation energy to a spatial target in the patient. Stimulation control circuit 1114 can control the delivery of the neurostimulation energy from stimulation output circuit 212. In various embodiments, stimulation control circuit 1114 can control the delivery of the neurostimulation energy, including the selection of the one or more stimulation electrodes, according to both sensing and therapeutic needs. The sensing needs includes evoking the neural responses to be analyzed for the one or more indications of the neurodegenerative disease.

Sensing circuit 1142 represents an example of sensing circuit 942 and includes a signal conditioning circuit 962 and a signal processing circuit 1164. When implantable stimulator 1104 is connected to lead(s) 708, signal conditioning circuit 942 is coupled to electrodes 706 to receive one or more neural signals from one or more sensing electrodes selected from electrodes 706 and to pre-condition the one or more neural signals for processing. In various embodiments, the one or more neural signals can be received and processed through one or more sensing channels each including a set of sensing electrodes selected for sensing a neural signal from a spatial target in the patient. In one embodiment, electrodes 706 are placed over the patient's spinal cord for delivering SCS and sensing one or more electrospinogram (ESG) signals. In various embodiments, implantable stimulator 1104 can deliver the neurostimulation energy and sense the one or more neural signals concurrently or simultaneously.

Signal processing circuit 1164 represents an example of signal processing circuit 964 and includes a detection circuit 1166 and an analysis circuit 1168. Detection circuit 1166 can detect one or more attributes of the neural responses. Example of the one or more attributes include neural conduction velocity (NCV) and a morphology of the neural responses. Analysis circuit 1168 can analyze, by executing an analysis algorithm, the detected one or more attributes of the neural responses for one or more indications of one or more neurodegenerative diseases. In various embodiments, analysis circuit 1168 can analyze the detected one or more attributes of the neural responses over time (e.g., producing and analyzing a trend for each of the one or more attributes) for a level of disease progression in the one or more neurodegenerative diseases. Examples of the one or more neurodegenerative diseases include peripheral neuropathies, diabetic neuropathy, chronic pain, Alzheimer's disease, Parkinson's diseases, and multiple sclerosis. In various embodiments, analysis circuit 1168 can to generate a disease detection alert in response to the one or more neurodegenerative diseases being indicated as an outcome of the analysis and/or a disease progression alert in response to the level of disease progression exceeds a threshold level. Analysis circuit 1168 can then transmit the detection and/or progression alerts to an external system (such as external system 502) via implant telemetry circuit 744.

Memory circuit 1146 can store data representing the detected one or more attributes of the neural responses. Storage of such data allows for the analysis of the detected one or more attributes of the neural responses over time (e.g., over different time spans such as seconds, minutes, hours, weeks, months, or years)

In various embodiments, signal processing circuit 1164 can detect and analyze NCV as an attribute of the neural responses. Detection circuit 1166 can include an NCV detection circuit to detect an NCV of the neural responses. The NCV detection circuit detects a time interval $\Delta t$ during which a detected feature of the neural signal (e.g., an evoked response in ESG) travels a known distance D (e.g., distance between stimulation and/or sensing electrode locations) and calculates the NCV by dividing D by $\Delta t$ (i.e., NCV=D/$\Delta t$). The NCV detection circuit can further calculate a variability range for the NCV.

In one embodiment, a stimulus is delivered from implantable stimulator 1104 or TENS unit 1070. The NCV detection circuit detects the evoked response using electrode 1 and electrode 2 selected from electrodes 706 and calculates the NCV using the equation NCV=D/(t2-t1), wherein D is the distance between electrode 1 and electrode 2, t1 is the time of detection of the evoked response using electrode 1, and t2 is the time of detection of the evoked response using electrode 2 ($\Delta t$=t2-t1).

In another embodiment, a stimulus is delivered from TENS device 1070. A surface stimulation electrode selected from electrodes 1072 is placed at site 1 and then site 2 for delivering the stimulus from TENS unit 1070 to site 1 and then to site 2. The NCV detection circuit detects the evoked response using an electrode selected from electrodes 706 and calculates the NCV using the equation NCV=D/(t2-t1), wherein D is the distance between site 1 and site 2, t1 is the time of detection of the evoked response resulting from the stimulation signal delivered site 1, and t2 is the time of detection of the evoked response resulting from the stimulation signal delivered site 2 ($\Delta t$=t2-t1).

In yet another embodiment: a stimulus is delivered from implantable stimulator 1104 or TENS unit 1070 using electrode 1 selected from electrodes 706 or electrodes 1072, respectively. The NCV detection circuit detects the evoked response by electrode 2 selected from electrodes 706, detects a temporal delay between the delivery of the stimulus using electrode 1 and the detection of the evoked response using electrode 2, and calculates the NCV using the equation NCV=D/t, wherein D is the distance between electrode 1 and electrode 2, and t is the temporal delay. Alternatively, because the conduction distance remains substantially unchanged, and the temporal delay inversely proportional to the NCV, the temporal delay can be used as a surrogate for the NCV without knowing D. Changes of the temporal delay over time is inversely proportional to changes in the NCV, and hence can be used to monitor the changes in the NCV.

Analysis circuit 1168 can include an NCV analysis circuit to analyze values of the detected NCV for an NCV-based indication of the one or more neurodegenerative diseases, and produce the disease detection alert in response to the neurodegenerative disease being indicated as an outcome of the analysis. The NCV analysis circuit can also analyze the values of the detected NCV over time for a level of disease progression in the one or more neurodegenerative diseases, and generates a disease progression alert in response to the level of disease progression being above a threshold level. In one embodiment, the NCV analysis circuit compares the NCV to an NCV threshold range and generates the disease detection or progression alert if NCV is outside the threshold range. The threshold range can be established to present a normal neural response and calibrated as needed (e.g., to accommodate changes in the patient's conditions).

In various embodiments, signal processing circuit 1164 can detect and analyze a morphology as an attribute of the neural responses. Detection circuit 1166 can include a morphology detection circuit to detect the morphology by detecting a neural response waveform or one or more morphological parameters representing the neural response waveform. Examples of the one or more morphological parameters include:

area under the curve (the area between the ESG signal and a baseline for an evoked response or another specified period, also referred to curve area in this document), which can be determined using:

$$A = \sum_{n=1}^{N} |y(n)|,$$

where A is the area under the curve, n is the time index, y is the data time series, and N is the index of the last data sample in the time series;

curve length (duration of an evoked response measured from the ESG signal which can be determined using:

$$CL = \sum_{n=2}^{N-1} |y(n) - y(n-1)|,$$

where CL is the curve length;

N1-to-P2 amplitude (the difference between amplitudes of N1 and P2, where N1 is the first negative peak in an evoked response that is correlated to the response of faster fibers such as Aβ fibers and myelinated fibers, and P2 is the second positive peak in the evoked response that is correlated with response of slower fibers); and variability range for each of these morphological parameters.

Analysis circuit 1168 can include a morphology analysis circuit to analyze the detected morphology for a morphology-based indication of the one or more neurodegenerative diseases, and produce the disease detection alert in response to the neurodegenerative disease being indicated as an outcome of the analysis. The morphology analysis circuit can also analyze changes of the detected morphology over time for a level of disease progression in the one or more neurodegenerative diseases, and generates a disease progression alert in response to the level of disease progression being above a threshold level. In one embodiment, the morphology analysis circuit compares the detected morphology to a stored template morphology by computing a correlation coefficient. The template morphology including data representing a template neural response waveform or a template value set for the one or more morphological parameters representing the neural response waveform. The morphology analysis circuit generates the disease detection or progression alert if the correlation coefficient is below a morphology threshold. The template morphology can be established to present a normal neural response and calibrated as needed (e.g., to accommodate changes in the patient's conditions). In one embodiment, a template morphology of the neural response (ECAP or full ESG) can be stored and correlated with morphologies of new neural responses that occur over time, using template matching techniques, cross-correlation, similarity measurements to assess the changes in the ECAP response caused for losses of myelin over time. An example of template matching technique is discussed in U.S. Pat. No. 7,539,536, assigned to Cardiac Pacemakers, Inc., which is incorporated by reference herein in its entirety.

In various embodiments, signal processing circuit 1164 can detect and analyze the NCV, the morphology, and/or one or more other attributes of the neural responses. Detection circuit 1166 can include the NCV detection circuit and/or the morphology detection circuit.

Figure 12:
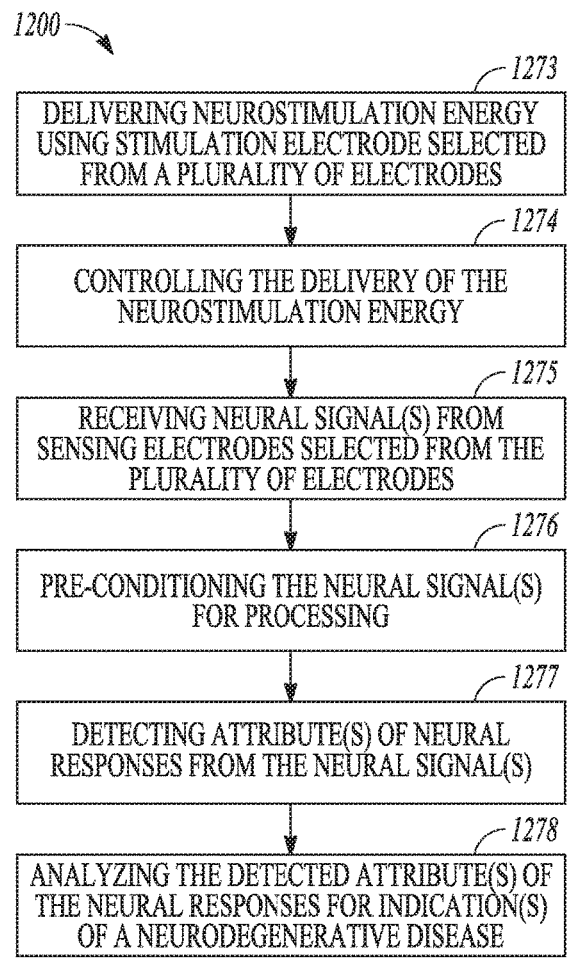
FIG. 12 illustrates an embodiment of a method for operating a neurostimulation system with disease detection capabilities.

FIG. 12 illustrates an embodiment of a method 1200 for operating a neurostimulation system with disease detection capabilities, such as neurostimulation system 1000. The neurostimulation system can include one or more processors programmed to perform selected or all the steps of method 1200. A non-transitory computer-readable storage medium can include instructions, which when executed by the one or more processors, cause the one or more processors to perform method 1200 for operating the neurostimulation system to deliver neurostimulation energy to a patient using a plurality of electrodes.

At 1273, the neurostimulation energy is delivered using stimulation electrodes selected from the plurality of electrodes. In various embodiments, the neurostimulation energy is delivered as electrical neurostimulation pulses from an implantable stimulator coupled to the stimulation electrodes. In some embodiments, the neurostimulation energy is also delivered as electrical neurostimulation pulses from a TENS unit through surface stimulation electrodes attached onto the patient to support the disease detection capabilities. This allows for examining nerves not accessible using the plurality of electrodes coupled to the implantable stimulator. At 1274, the delivery of the neurostimulation energy is controlled, for example, to support the disease detection capabilities.

At 1275, one or more neural signals are received from sensing electrodes selected from the plurality of electrodes. In one embodiment, the neurostimulation system is an SCS system that includes an implantable stimulation coupled to the plurality of electrodes placed in the patient over the spinal cord. The one or more neural signals include one or more ESG signals with the neural responses including ECAPs. At 1276, the one or more neural signals are pre-conditioned for processing. The pre-conditioning can include amplification and/or filtering.

At 1277, one or more attributes of neural responses are detected from the one or more neural signals. In various embodiments, the neural responses are each evoked by a pulse of the electrical neurostimulation pulses. In various embodiments, the one or more attributes can include NCV, morphology, and/or one or more other attributes of the neural responses. The morphology to be detected can include a neural response waveform or one or more morphological parameters representing the neural response waveform. At 1278, the detected one or more attributes of the neural responses are analyzed for one or more indications of a neurodegenerative disease. This can include comparing the detected NCV to an NCV threshold range for an NCV-based indication of the one or more indications of one or more neurodegenerative diseases and/or comparing the detected morphology to a stored template morphology for a morphology-based indication of the one or more indications of one or more neurodegenerative diseases.

In various embodiments, method 1200 can be performed repeatedly over time to track progression of the neurodegenerative disease. Changes in the NCV and/or changes in the morphology of the neural responses over time can be used to assess level of neural transmission deterioration in nerve fibers. In various embodiments, the NCV and/or morphology can be detected before and after a delivery of therapy for treating neuropathy (abnormal neural transmission) to monitor effectiveness of the therapy. The outcome of analysis of the detected NCV and/or morphology can be used, for example, to adjust the dosage of medication when the therapy is a drug therapy and/or to adjust stimulation parameters when the therapy is a neurostimulation therapy.

In various embodiments, method 1200 can be performed for a preventive check of health of the patient's nervous system. Health check of nervous system can be performed by monitoring changes in the NCV and/or morphology of the neural responses for indications of presence or progression of the neurodegenerative disease.

Figure 13:
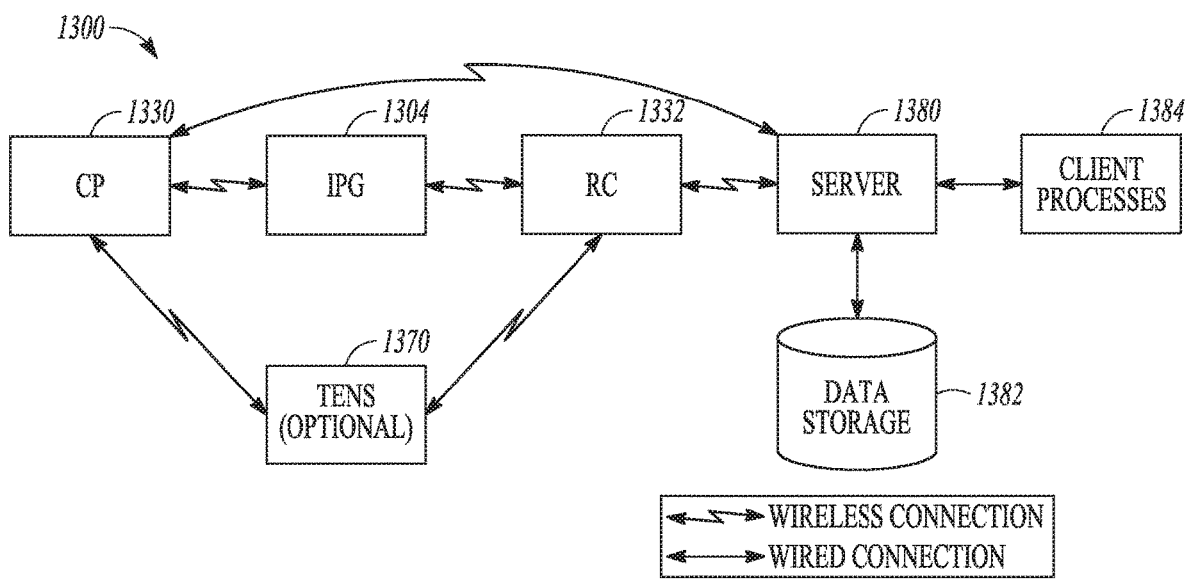
FIG. 13 illustrates an embodiment of a diagnostic system that includes a neurostimulation system with disease detection capabilities, such as the neurostimulation system of FIG. 10.

FIG. 13 illustrates an embodiment of a diagnostic system 1300 that includes a neurostimulation system with disease detection capabilities, such as neurostimulation system

1000. System 1300 can represent an example of adding disease detection capabilities, such as those of system 1000, to a neurostimulation system, such as system 100, 500, and 600, that communicates with a server or network allowing clinical personnel and other authorized personnel (e.g., researchers and representatives of a stimulation device manufacturer) to participate in therapeutic and/or diagnostic processes.

System 1300 can include an IPG 1304, a CP 1330, an RC 1332, a TENS unit 1370 (optional), a server 1380, a data storage 1382, and client processes 1384. IPG (or implantable stimulator) 1304 can be an example of IPG 504 configured to deliver neurostimulation therapy and perform diagnostic sensing including trending acquired diagnostic data and generating disease detection and/or progression alerts (e.g., to operate as implantable stimulator 1104). IPG 1304 can wirelessly communicate with CP 1330 and RC 1332, including uploading the alerts to server 1380 via CP 1330 and/or RC 1332.

CP 1304 can be an example of CP 604 configured to support the disease detection capabilities of system 1300, including programming IPG 1304 for controlling the delivery of the neurostimulation therapy and performance of the diagnostic sensing. CP 1304 can be implemented as a dedicated device or using any computing device with a user interface, such as a desktop computer, a laptop computer, a tablet device, or a mobile device. RC 1332 can be an example of RC 632 configured to support the disease detection capabilities of system 1300, including allowing the patient to control the delivery of the neurostimulation therapy and initiate certain diagnostic processes, and to present selected or all the disease detection and/or progression alerts to the patient. RC 1332 can be implemented as a dedicated handheld device or an application in a smart phone. CP 1330 and RC 1332 can each wirelessly communicate with server 1380 to upload the diagnostic data and the alerts received from IPG 1304 to server 1380. In some embodiments, CP 1330 and/or RC 1332 can also process the diagnostic data received from IPG 1304 (e.g., for presentation to the user and/or the patient) and upload the processed diagnostic data to server 1380. TENS unit 1370 is optionally included in system 1300 and used to deliver the neurostimulation energy to nerve targets not accessible by IPG 1304 using implantable lead(s).

Client processes 1384 can include processing of the diagnostic data uploaded to server 1380. Examples of the processing include analysis, trending, alert generation, and diagnostic report generation related to detection or progression of neurodegenerative disease in the patient and/or results of health check of the patient's nervous system. Client processes 1384 can also include functioning related to a diagnostic database, such as searches of data stored in data storage 1382. Client processes 1384 can also include communications such as sending alerts to various recipients including the patient and those participating in the treatment of the patient via e-mail and/or telephone, providing the patient's care provider with access to diagnostic reports, and updating application(s) in CP 1330 and/or RC 1332 based on the diagnostic reports when needed. Data storage 1382 can store data received by server 1380 and allow for retrieval as needed. The stored data can include data uploaded from CP 1330 and/or RC 1332 and data resulting from the diagnostic data processing and communications performed by client processes 1384. Examples of such stored data include raw data acquired by IPG 1304, diagnostic metrics resulting from processing the raw data by IPG 1304, CP 1330, RC 1332, and/or client processes 1384, trends, alerts (including history), and the diagnostic reports.

Figure 14:
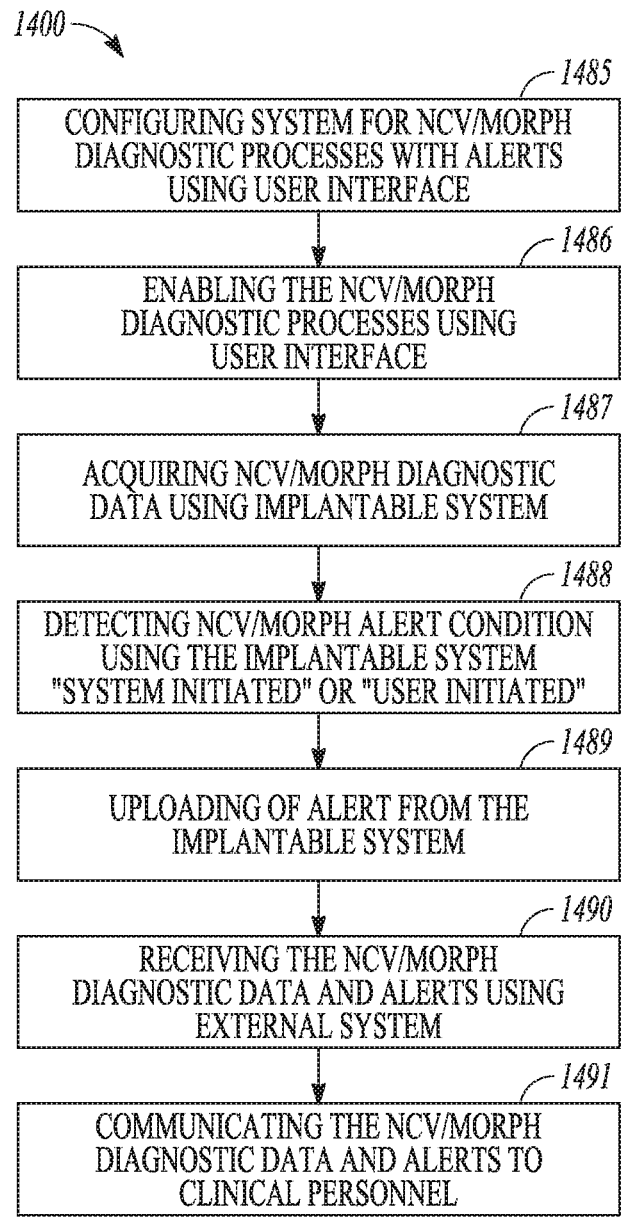
FIG. 14 illustrates an embodiment of a method for operating a neurostimulation system, such as the neurostimulation system of FIG. 13.

FIG. 14 illustrates an embodiment of a method 1400 for operating a neurostimulation system such as system 1300. Method 1400 is discussed as an example illustrating how system 1300 can be used rather than any limitation on that system 1300 can do or how it can be used. While the NCV and/or morphology of the neural responses ("NCV/MORPH" in FIG. 14) are used as an example, method 1400 can use any one or more attributions of the neural responses that can be analyzed to indicate neurodegenerative diseases and their progression.

At 1485, the neurostimulation system is configured for NCV/Morph diagnostic processes with alert generation using a user interface, such as the user interface of CP 1330. At 1486, the NCV/Morph diagnostic processes is enabled using a user interface, such as the user interface of CP 1330 or RC 1332.

At 1487, NCV/Morph diagnostic data are acquired using an implantable system, such as IPG 1304 coupled to implantable lead(s). At 1488, an alert condition is detected from the NCV/Morph diagnostic data using the implantable system. In various embodiments, an alert can be automatically generated by the system upon detection of the alert condition (e.g., an NCV/Morph parameter exceeding a threshold) and/or can be generated in response to a command received from a user (e.g., the patient or a physician or other caregiver attending the patient) using CP 1330 or RC 1332 (e.g., when the patient experiences a symptom). At 1489, the alert is uploaded from the implantable system.

At 1490, the NCV/Morph diagnostic data and alerts are received using an external system (e.g., server 1380). At 1491, the NCV/Morph diagnostic data and alerts are communicated to clinical personnel using the external system.

Figure 15A:
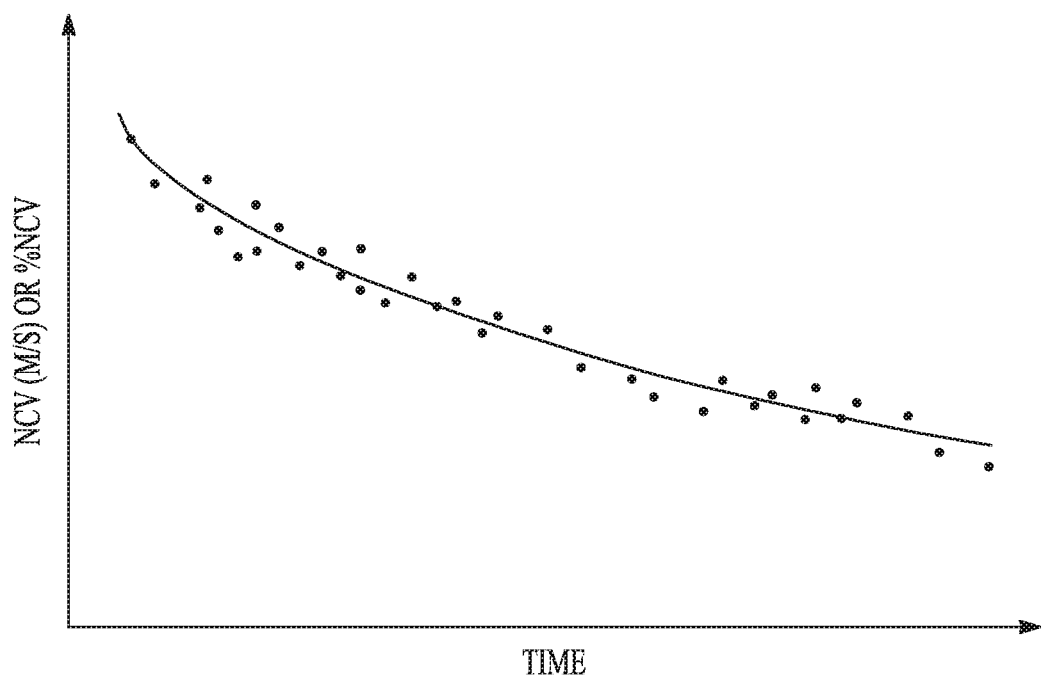
FIGS. 15A-B each illustrate an embodiment of a presentation of diagnostic information acquired using a neurostimulation system, such as the neurostimulation system of FIG. 13.
Figure 15B:
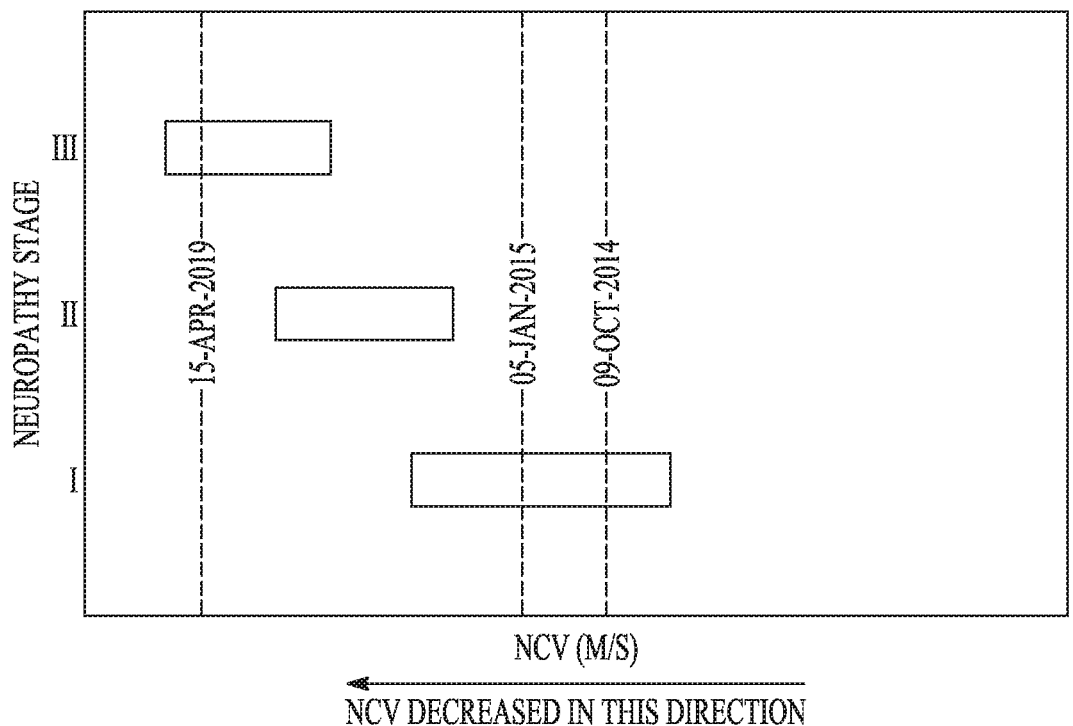

FIGS. 15A-B each illustrate an embodiment of a presentation of diagnostic information acquired using a neurostimulation system such as system 1300. For example, the presentation can be made using the user interface of CP 1330 and/or a user interface used in client processes 1384. FIG. 15A illustrates a graph of NCV (or % NCV showing relative changes in the NCV) plotted against time. FIG. 15B illustrates neuropathy stage plotted against the patient's NCV shown dates of assessment marked at the NCV measured on that date. NCV can be considered as the most objective assessment of nerve function, that is also sensitive and repeatable; hence, it is a useful indicator of neuropathies. This is particularly true to diabetic neuropathy, where the disease progression causes a decrease in the NCV produced by demyelination of fibers and eventually loss of large myelinated axons, but is also applicable to other neurodegenerative diseases. The changes in the NCV can be observed over a period spanning several months to years. The longer the time the more disease progression is observed, the higher the likelihood is to have the subject shift to the next disease stage. Besides the NCV, the morphology of the evoked response of the fibers also changes and typically decreases its amplitude over time and presents other morphological changes observable or extractable from the evoked response. These changes do not occur overnight, but rather slowly, and advanced signal processing techniques can enable a more refined tracking of the NCV and morphology changes in the evoked response to allow early detection in diabetic patients that are using an implanted neurostimulation system or to guide effectiveness of drug therapy treatments for this or other neurodegenerative diseases.

Figure 16:
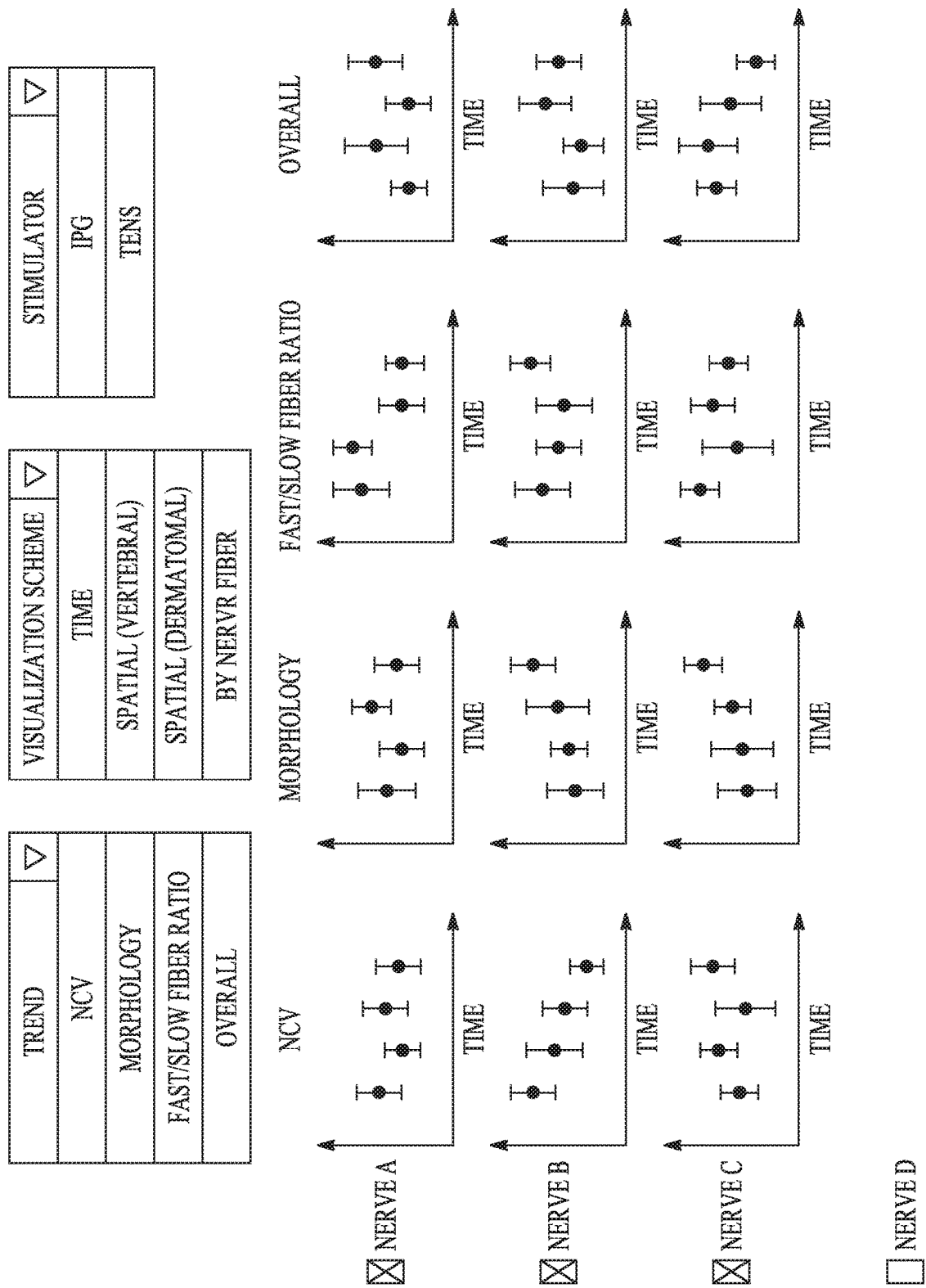
FIG. 16 illustrates an embodiment of portions of a user interface providing for user-controllable presentation of diagnostic information acquired using a neurostimulation system, such as the neurostimulation system of FIG. 13.

FIG. 16 illustrates an embodiment of portions of a user interface providing for user-controllable presentation of diagnostic information acquired using a neurostimulation system such as system 1300. The user interface can be the user interface of CP 1330 and/or a user interface used in client processes 1384. In the illustrated embodiment, user inputs controlling the presentation includes selection of nerve(s) (one or more from nerves A-D as shown) and pull-down menus for selecting trend, visualization scheme, and stimulator. The trend can be selected from NCV, morphology, fast/slow fiber ratio, and overall (all selected as shown by the displayed data). The fast/slow fiber ratio is a ratio of the amount of fibers with fast NCV to the amount of fibers with slow NCV. The "overall" is a weighted combination of the NCV, morphology, fast/slow fiber ratio, and/or other trends that provide an overall trend change of disease progression. It can be patient-specific as different patients may show that have trends that are more sensitive to disease progression than others. Other examples of trends, not shown in FIG. 16 but known to those skilled in the art, can include changes in power in specified frequency bands of the evoked response, the ratio of the power from different frequency bands, the changes in the cross-correlation of the evoked response at different times, and any metric indicative of changes in the morphology of the evoked response signal. The visualization scheme can be selected from time, spatial (vertebral), spatial (dermatomal), and by nerve fiber (time selected as shown by the displayed data). The stimulator can be selected from IPG and TENS (selection not reflected in the displayed data).

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation energy to a patient using a plurality of electrodes, the system comprising:
    a stimulation circuit configured to deliver neurostimulation pulses using stimulation electrodes selected from the plurality of electrodes and to control the delivery of the neurostimulation pulses; and
    a sensing circuit configured to receive one or more neural signals from sensing electrodes selected from the plurality of electrodes and including a signal processing circuit including:
        a detection circuit configured to detect one or more attributes of evoked responses from the received one or more neural signals, the evoked responses each being a neural response evoked by a pulse of the neurostimulation pulses; and
        an analysis circuit configured to analyze the detected one or more attributes of the evoked responses for one or more indications of a neurodegenerative disease.

2. The system of claim 1, further comprising a memory circuit configured to store the detected one or more attributes of the evoked responses, and wherein the analysis circuit is further configured to analyze the detected one or more attributes of the evoked responses over time for a level of disease progression in the neurodegenerative disease.

3. The system of claim 2, wherein the analysis circuit is further configured to generate at least one of a disease alert or a disease progression alert, the disease alert to be generated in response to the neurodegenerative disease being indicated as an outcome of the analysis, the disease progression alert to be generated in response to the level of disease progression being above a threshold level.

4. The system of claim 1, wherein the stimulation circuit is configured to deliver spinal cord stimulation, the sensing circuit is configured to sense one or more electrospinogram signals, and the detection circuit is configured to detect a morphology of the evoked responses.

5. The system of claim 1, comprising an implantable stimulator including the stimulation circuit and the sensing circuit.

6. The system of claim 5, further comprising a transcutaneous electrical nerve stimulation (TENS) device including surface stimulation electrodes configured to be attached onto the patient, wherein the TENS device is configured to deliver external stimulation pulses using the surface stimulation electrodes, and the detection circuit is further configured to detect neural responses each evoked by a pulse of the external stimulation pulses.

7. The system of claim 1, wherein the detection circuit is configured to detect a neural conduction velocity (NCV) of the evoked responses.

8. The system of claim 7, wherein the detection circuit is configured to detect the NCV by detecting at least one of a time interval during which a detected feature of the evoked responses travels a known distance or a time interval between a response of the detected evoked responses and the pulse evoking that response, and the analysis circuit is configured to compare the detected NCV to an NCV threshold range for an NCV-based indication of the one or more indications of one or more neurodegenerative diseases.

9. The system of claim 1, wherein the detection circuit is configured to detect a morphology of the evoked responses, the morphology to be detected including an evoked response waveform or one or more morphological parameters representing the evoked response waveform.

10. The system of claim 9, wherein the analysis circuit is configured to compare the detected morphology to a stored template morphology for a morphology-based indication of the one or more indications of one or more neurodegenerative diseases.

11. A method for operating a system configured for delivering neurostimulation energy to a patient using a plurality of electrodes, the method comprising:
    delivering neurostimulation pulses using stimulation electrodes selected from the plurality of electrodes;
    controlling the delivery of the neurostimulation pulses;
    receiving one or more neural signals from sensing electrodes selected from the plurality of electrodes;
    detecting one or more attributes of evoked responses from the one or more neural signals, the evoked responses each being a neural response evoked by a pulse of the neurostimulation pulses; and
    analyzing the detected one or more attributes of the evoked responses for one or more indications of a neurodegenerative disease.

12. The method of claim 11, further comprising performing the method for a preventive check of health of the patient's nervous system.

13. The method of claim 11, further comprising performing the method repeatedly over time to track progression of the neurodegenerative disease.

14. The method of claim 11, wherein delivering the neurostimulation energy comprises delivering the neurostimulation pulses from an implantable stimulator coupled to the stimulation electrodes selected from the plurality of electrodes.

15. The method of claim 11, wherein delivering the neurostimulation energy comprises delivering the neurostimulation pulses from at least one of an implantable stimulator coupled to the stimulation electrodes selected from the plurality of electrodes or a transcutaneous electrical nerve stimulation (TENS) device including surface stimulation electrodes configured to be attached onto the patient.

16. The method of claim 11, wherein detecting the one or more attributes of the evoked responses comprises detecting a neural conduction velocity (NCV).

17. The method of claim 16, wherein detecting the NCV comprises detecting at least one of a time interval during which a detected feature of the evoked responses travels a known distance or a time interval between a response of the detected evoked responses and the pulse evoking that response, and analyzing the detected one or more attributes of the evoked responses comprises comparing the detected NCV to an NCV threshold range for an NCV-based indication of the one or more indications of one or more neurodegenerative diseases.

18. The method of claim 11, wherein detecting the one or more attributes of the neural evoked responses comprises detecting a morphology of the evoked responses, the morphology to be detected including an evoked response waveform or one or more morphological parameters representing the evoked response waveform.

19. The method of claim 18, wherein analyzing the detected one or more attributes of the evoked responses comprises comparing the detected morphology to a stored template morphology for a morphology-based indication of the one or more indications of one or more neurodegenerative diseases.

20. A non-transitory computer-readable storage medium including instructions, which when executed by a machine, cause the machine to perform a method for operating a system configured for delivering neurostimulation energy to a patient using a plurality of electrodes, the method comprising:

delivering neurostimulation pulses using stimulation electrodes selected from the plurality of electrodes;

controlling the delivery of the neurostimulation pulses;

receiving one or more neural signals from sensing electrodes selected from the plurality of electrodes;

detecting one or more attributes of evoked responses from the one or more neural signals, the evoked responses each being a neural response evoked by a pulse of the neurostimulation pulses; and analyzing the detected one or more attributes of the evoked responses for one or more indications of a neurodegenerative disease.

* * * * *